(12) United States Patent
Knopfle

(10) Patent No.: US 7,927,098 B2
(45) Date of Patent: Apr. 19, 2011

(54) SURGICAL ANCHOR DEVICE

(75) Inventor: Christian Knopfle, Donaueschingen (DE)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 680 days.

(21) Appl. No.: 11/209,129

(22) Filed: Aug. 22, 2005

(65) Prior Publication Data
US 2006/0069389 A1 Mar. 30, 2006

(30) Foreign Application Priority Data

Sep. 24, 2004 (DE) .......................... 10 2004 046 414

(51) Int. Cl.
*A61C 3/00* (2006.01)
(52) U.S. Cl. ........................................................ 433/18
(58) Field of Classification Search .............. 433/17–24, 433/173, 174, 176; 623/17.17–17.19; 606/61, 606/70
See application file for complete search history.

(56) References Cited

U.S. PATENT DOCUMENTS

| 6,575,742 | B2 | 6/2003 | Kyung et al. | |
| 6,726,473 | B1 * | 4/2004 | Guray | 433/6 |
| 2004/0067464 | A1 * | 4/2004 | Lin | 433/18 |
| 2004/0147931 | A1 * | 7/2004 | De Clerck | 606/70 |

FOREIGN PATENT DOCUMENTS

| DE | 203 10 648 U 1 | 11/2003 |
| EP | 0823244 | 8/1997 |
| JP | 2004057729 | 2/2004 |
| WO | WO 02/02023 | 1/2002 |
| WO | WO 02/91941 | 5/2002 |

OTHER PUBLICATIONS

EP International Search Report, International Application No. EP 05012535.0-2318; International Filing Date Dec. 8, 2005.
English Abstract for Japanese Patent 2004057729.

* cited by examiner

*Primary Examiner* — Cris L Rodriguez
*Assistant Examiner* — Sunil K Singh
(74) *Attorney, Agent, or Firm* — Howard & Howard Attorneys PLLC

(57) ABSTRACT

An orthodontic anchor device (10) for a surgical traction element is described. The anchor device includes a fixing device (12), which can be fixed in or to a bone in the mouth region, as well as a clamping device (18) coupled to the fixing device (12). The clamping device (18) has at least one locating region for the traction element as well as an oblique surface which can rotate relative to the locating region or which co-operates with a rotatable element. In order to produce a clamping force which fixes the traction element, a relative rotation takes place between the oblique surface and the rotatable element or between the oblique surface and the locating region.

26 Claims, 5 Drawing Sheets

SURGICAL ANCHOR DEVICE

FIELD OF THE INVENTION

The invention relates to a device for anchoring a surgical traction element in the mouth region. Anchor devices of this kind are frequently used for orthodontic purposes.

BACKGROUND OF THE INVENTION

The object of orthodontic operations is to treat tooth irregularities. Tooth irregularities are often treated by exerting tractive or compressive forces on the teeth which are to be treated. For this purpose a first end of a surgical element for exerting a tractive or compressive force (called a traction element in the following for the sake of simplicity) is fastened to a tooth which is to be treated. The other end of the traction element was in the past frequently fixed to another tooth. However the disadvantage in this respect is that this other tooth also gradually changes its position on account of the counterforce acting on it. This is undesirable in most cases.

This was the reason for the development of anchor devices so as to avoid having to fasten the free end of a traction element fastened to a tooth which is to be treated to another tooth. As a rule, anchor devices of this kind comprise a fixing device which can be fixed in or to a bone as well as a retaining device, coupled to the fixing device, for the traction element.

An anchor device of this kind is known from WO 02/02023 A, for example. The known anchor device has a fixing device in the form of a linear bone plate which is fastened on a jaw-bone by means of suitable bone screws. The bone plate is connected to a hook-like retaining device for a traction element.

A further anchor device is described in WO 02/091941 A. The anchor device in the latter likewise comprises a fixing device in the form of a bone plate as well as a retaining device connected to the bone plate (by means of an L-shaped intermediate piece). The retaining device has a spherical head through which two through-openings pass, these extending perpendicularly to one another. The through-openings function as a locating region for a traction element having the shape of a wire, for example. A clamping force which fixes the traction element in the through-openings can be produced by means of a clamping screw extending perpendicularly to the through-openings.

An anchor device which is known from EP 0 823 244 A has a fixing device in the form of a pin or a screw which can be fastened directly in a bone. A hook is provided as retaining device for the traction element, which hook is retained at a spacing from the fixing device by means of an arm.

A further anchor device with a fixing device formed as a bone screw is described in U.S. Pat. No. 6,575,742 B. This anchor device comprises a screw head, extending co-linearly with the bone screw, with a retaining device for the traction element. The retaining device is formed as a through-opening which passes through the screw head perpendicularly to the screw shank. The screw head also has a circumferential depression for fastening a traction element in the form of a wire loop or a rubber band.

The object underlying the invention is to provide a device for anchoring a surgical traction element in the mouth region which can be easily handled.

SUMMARY OF THE INVENTION

This object is achieved by a device for anchoring a first surgical traction element in the mouth region, comprising a fixing device, which can be fixed in or to a bone, as well as a clamping device, coupled to the fixing device, with at least one locating region for the first traction element and with an oblique first surface which can rotate relative to the locating region or co-operates with a rotary element, so that a clamping force which fixes the first traction element can be produced by a relative rotation between the oblique first surface and the locating region or the rotary element.

The oblique first surface may co-operate indirectly (e.g. via an element which can move relative to the oblique surface) or directly with the traction element which is to be fixed. It may be formed in the region of a front face of a substantially annular, cylindrical or hollow cylindrical structure. The front face does not necessarily have to be an end face of the structure. The front face may rather, for example, also be formed in the region of an opening of the shell or mantle of a hollow cylindrical structure. According to a variant of the invention, the oblique first surface extends in the circumferential direction of the structure over at most approximately 360° or at most approximately 270° of the front face. This means that the first surface does not in this case extend like a helix.

The clamping device may have a rotary element which can rotate relative to the locating region and at which the first surface is formed. The rotary element expediently has a suitable structure (e.g. an internal or external polygon, a recess or cross recess, etc.) which facilitates the introduction of a torque into the rotary element.

In addition to the oblique first surface, the clamping device may have a second surface which extends obliquely to the first surface and co-operates with the oblique first surface. The co-operation may take place such that an advance movement giving rise to the clamping force can be produced when the two surfaces rotate relative to one another. This advance movement may relate to the structure at which the first surface or the second surface is formed. If, for example, the second surface is supported so as to be non-rotatable relative to the locating region, a rotation of the structure at which the first surface is formed can give rise to an axial advance movement of the structure provided with the second surface along the axis of rotation (or vice versa).

The clamping device may comprise a separate clamping element at which the oblique second surface is formed. The clamping element may have a substantially annular, cylindrical or hollow cylindrical form, and the second surface may be formed at a front face of the clamping element. It is expedient for the clamping element to be disposed functionally between the first surface and the locating region and to co-operate indirectly or directly with the traction element which is to be fixed.

The anchor device according to the invention may also comprise a head which is retained (e.g. by the fixing device or an intermediate piece) at a spacing from the bone and at which the clamping device is formed. According to a first variant, the head is a direct (e.g. rectilinear) prolongation of the fixing device. According to a second variant, the head is coupled to the fixing device by means of an (integral or non-integral) intermediate piece. The intermediate piece may be bent.

The head may have a (e.g. circular ring-shaped) diametrical widening extending substantially parallel to the bone and belonging to the locating region for the traction element which is to be fixed. At least one groove, which extends substantially in a plane parallel to the bone, may also be formed in the region of the head. The groove may extend in the circumferential direction of the head or perpendicularly thereto. It may be used to suspend the first or a second traction element. The groove expediently forms at least a part of the locating region.

The locating region may comprise one or a plurality of opening(s) passing through the head to introduce and/or pass through the first traction element. The one ora plurality of opening(s) may extend in a plane which is substantially parallel to the bone or obliquely thereto.

The fixing device may be configured in various ways. According to a first variant, the fixing device comprises a bone plate with at least one through-opening for a fastening element. The head, provided with the clamping device, of the anchor device may extend perpendicularly to the bone plate. For this purpose an intermediate piece bent substantially in the shape of an L may be provided between the head and the bone plate. The bone plate may have a T-, Y-, I- or V-shaped form or a form differing therefrom.

According to a second variant, the fixing device comprises a bone screw thread which can be screwed into a bone in a manner similar to that in U.S. Pat. No. 6,575,742 B initially mentioned. The bone screw thread may extend co-linearly with the axis of rotation of the relative rotation (between the locating region and the oblique first surface) in order to produce the clamping force.

According to a further aspect of the invention, an anchor system for a surgical traction element is provided. In addition to the anchor device, the anchor system comprises the first traction element and, optionally, a second traction element. The first traction element may be a wire, and the second traction element may be an elastic band or an elastic ring.

A preferred field of use for the device according to the invention and the system according to the invention is that of orthodontics. Alternative uses (also outside the mouth region) are possible.

BRIEF DESCRIPTION OF THE DRAWINGS

Further details and advantages of the invention will emerge from the following description of two embodiments and from the figures, in which.

DESCRIPTION OF PREFERRED EMBODIMENTS

The invention is illustrated in detail in the following on the basis of two embodiments. Elements which correspond to one another have been given corresponding reference numbers.

Figure 1:
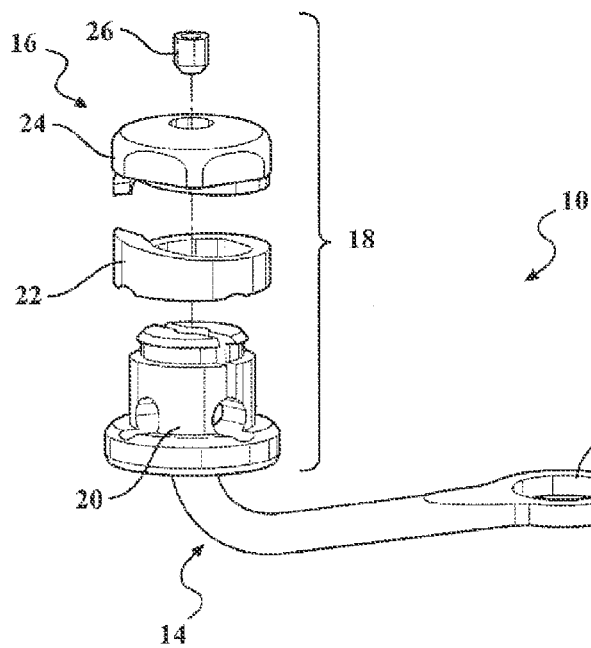
FIG. 1 shows a first embodiment of an anchor device according to the invention in an exploded representation.

FIG. 1 shows a first embodiment of an anchor device 10 according to the invention in an exploded representation. The anchor device 10 comprises a fixing device, which can be fixed to a bone, in the form of a bone plate 12 as well as a head 16 coupled to the bone plate 12 via an L-shaped intermediate piece 14. A clamping device 18, which consists of a plurality of components, is formed at the head 16. To be more precise, the clamping device 18 comprises a plurality of locating regions for traction elements (without reference numbers in FIG. 1) which are formed at a base body 20 of the head 16, a clamping element 22, a rotary element 24 formed as a cap as well as a locking bolt 26. The structure of these components as well as their mode of operation are explained in detail in the following.

As can be seen in FIG. 1, the bone plate 12 is of a linear (I-shaped) form with three through-openings 28 disposed one behind the other. Each of these through-openings 28 serves to locate a bone screw (not represented) for fixing the bone plate 12 to a bone. Differing from the construction which is represented in FIG. 1, the through-openings 28 of the bone plate 12 could alternatively be of any other desired arrangement (e.g. L-, T, or Y-shaped). It has proved to be expedient, in the case of a fixing device formed as a bone plate 12, is to provide at least three through-openings in order to enable the anchor device to be fixed to a bone (by means of at least two or—better—at least three fastening screws). The bone plate 12 is of a length of typically approximately 8 to approximately 20 mm. The bones screws which are used to fasten the bone plate 12 to a bone typically have a thread diameter in the range between approximately 1.5 and approximately 2.5 mm and a head diameter of typically approximately 2.7 to approximately 5 mm.

Figure 2:
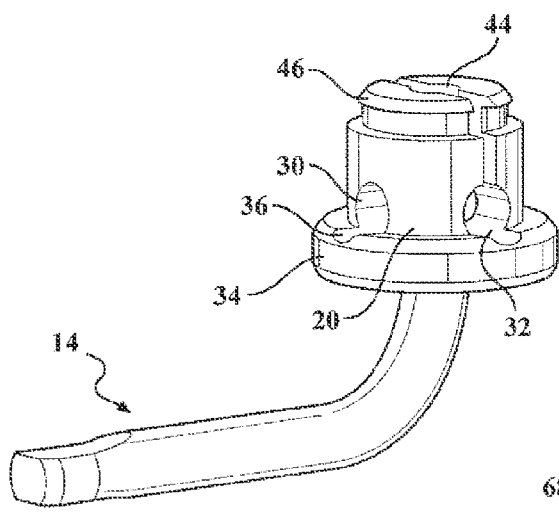
FIG. 2 is a perspective view of a head base body and an intermediate piece of the anchor device according to FIG. 1.

FIG. 2 is a perspective view of the base body 20 of the head 16 and of the intermediate piece 14 formed as an L-shaped stem. The base body 20 and the intermediate piece 14 are made of a single machined part. The length of the intermediate piece 14 is in the range between approximately 5 and approximately 15 mm. On account of its L-shape, the intermediate piece 14 retains the base body 20 and therefore also the head 16 of the anchor device 10 at a spacing of between approximately 2 and 7 mm from the bone. The free end of the intermediate piece 14 is welded to the bone plate 12 when the anchor device 10 is assembled.

Figure 3:
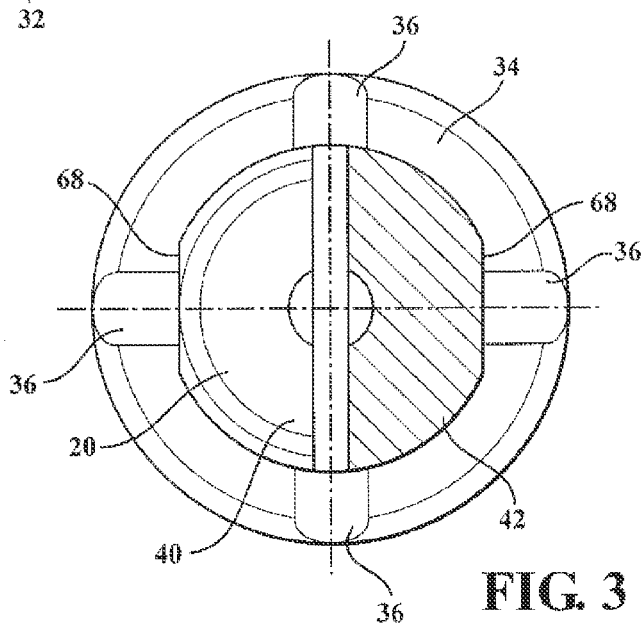
FIG. 3 is a plan view onto the base body according to FIG. 2 in a part-sectional representation.

According to FIG. 2, the base body 20 comprises a plurality of locating regions for the traction element which is to be fixed to the anchor device 10. These locating regions comprise two openings 30, 32 which extend perpendicularly to one another and pass through the base body 20 in a plane which is parallel to the bone plate 12. The base body 20, which is substantially cylindrical, also has a discoid diametrical widening 34 which likewise functions as a locating region. As can best be seen from FIG. 3, which is a plan view onto the base body 20, a total of four groove-shaped depressions 36 are formed in the diametrical widening 34 (as prolongations of the openings 30, 32). Just like the diametrical widening 34, these groove-shaped depressions 36 extend substantially parallel to the bone and to the bone plate 12. They likewise function as locating regions for a fixing traction element.

The diameter of the diametrical widening 34 is selected such that, when the clamping device 18 is completely assembled, the diametrical widening 34 projects radially beyond the other components of the clamping device 18 (in particular beyond the clamping element 22 and the rotary element 24), i.e. that the groove-shaped depressions 36 can still be seen by the surgeon when the head 16 is viewed from above. This visibility of the groove-shaped depressions 36, which represent the prolongations of the openings 30, 32, make it easier for the surgeon looking at the anchor device 10 to find the openings 30, 32 for introducing a traction element.

The base body 20 is split into two halves 40, 42 and has an axial opening 44 for introducing the locking bolt 26. The base body 20 also comprises a circumferential lip 46 at its end which is at the top in FIG. 2. This lip 46 is engaged with a complementary structure on the inside of the rotary element 24 when the clamping device 18 is in the assembled state, i.e. when the locking bolt 26 is introduced into the opening 44. The rotary element 24 (and therefore also the clamping element 22) is thus permanently connected to the base body 29. Details in this respect are explained further below with reference to FIG. 10.

Figure 4:
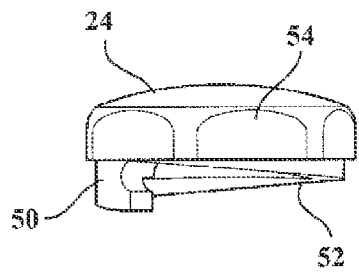
FIG. 4 is a side view of a rotary element of the anchor device according to FIG. 1.
Figure 5:
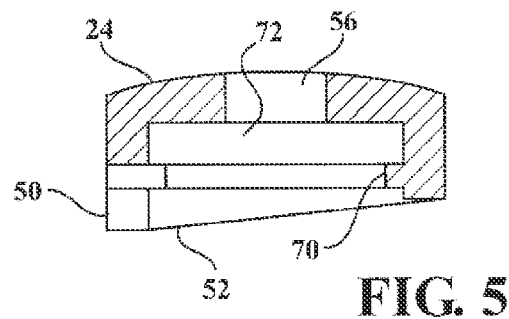
FIG. 5 is a sectional representation of the rotary element according to FIG. 4.

FIG. 4 is a side view and FIG. 5 a sectional view of the rotary element 24. The rotary element 24 is formed as a cap and has a substantially hollow cylindrical structure 50 at its end which is at the bottom in FIGS. 4 and 5. The hollow cylindrical structure 50 has an obliquely extending surface 52 at its free front side. The oblique surface 52 extends over approximately 360° of the front side of the hollow cylindrical structure 50 like a helix (although this would not be a screw thread).

As can be seen in FIG. 4, the rotary element 24 has an external polygon 54 so that a torque can be introduced into the rotary element 24. The rotary element 24 also has an opening 56 extending along its longitudinal axis. This opening 56 enables the locking bolt 26 to be passed through.

Figure 6:
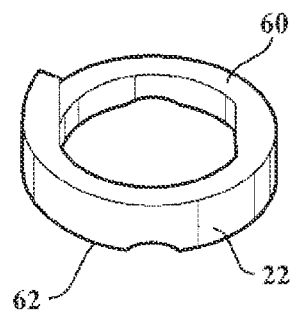
FIG. 6 is a perspective view of a clamping element of the anchor device according to FIG. 1.
Figure 7:
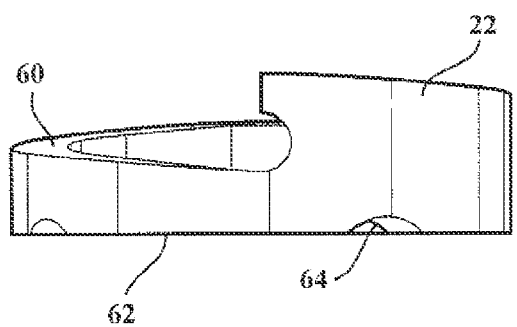
FIG. 7 is a side view of the clamping element according to FIG. 6.
Figure 8:
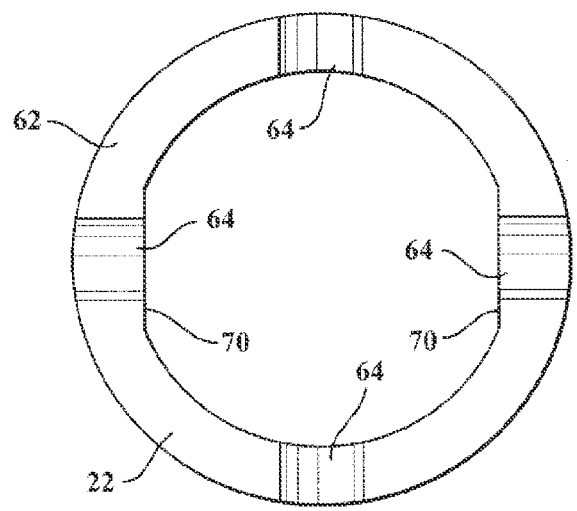
FIG. 8 is a view from below of the clamping element according to FIG. 6.

FIGS. 6 to 8 are various views of the clamping element 22. The clamping element 22 has an annular or a hollow cylindrical structure. The clamping element 22 is provided with an oblique surface 60 at its front side which faces the rotary element 24 in the assembled state, while the opposite front side 62 extends in a substantially plane manner. In the embodiment under consideration the terms "oblique" and "plane" relate to the orientation of the locating region or of the located traction element.

Four milled-out parts 64 are provided in the plane front side 62 of the clamping element 22 along two straight lines extending perpendicularly to one another. When the clamping device 18 is in the assembled state, the radial position of these milled-out parts 64 corresponds to the position of the groove-shaped depressions 36 of the diametrical widening 34 of the base body 20. In other words, in the assembled state the milled-out parts 64 likewise form a prolongation of the openings 30, 32 passing through the base body 20. In order to guarantee correct positioning of the milled-out parts 64 relative to the groove-shaped depressions 36 and the openings 30, 32, the clamping element 22 can be mounted positively on the base body 20 with a defined orientation. In order to obtain the positive engagement, the clamping element 22 and the base body 20 have complementary flattened portions 68 (FIG. 3) and 70 (FIG. 8) on two opposite sides in each case. The positive engagement at the same time results in the clamping element 22 (and therefore the oblique surface 60 thereof) being non-rotatably supported relative to the base body 20 (and therefore also relative to the individual locating regions). It is nevertheless still possible for the clamping element 22 to be axially displaced along the longitudinal axis of the base body 20 and along an axis of rotation of the rotary element 24. The significance of these circumstances is explained in detail further below when describing the mode of operation of the anchor device 10 according to the first embodiment.

Figure 9:
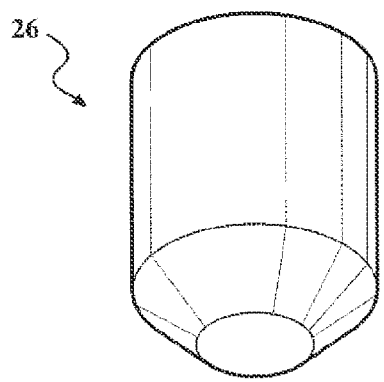
FIG. 9 shows a locking bolt of the anchor device according to FIG. 1.

FIG. 9 is a perspective view of the locking bolt 26, which is used when assembling the clamping device 18. As represented in FIG. 1, in order to assemble the clamping device 18, the clamping element 22 is firstly mounted positively on the base body 20 such that its oblique surface 60 points away from the diametrical widening 34 of the base body 20. The positive connection between the base body 20 and the clamping element 22 is formed such that the clamping element 22 is supported on the base body 20 such that it cannot rotate, yet can be displaced in the axial direction. The rotary element 24 is mounted on the base body 20 in a next step. The clamping element 22 is therefore disposed between the diametrical widening 34 of the base body 20 and the rotary element 24.

The rotary element 24 is mounted on the base body 20 such that the circumferential lip 46 of the base body 20 is disposed in a space 72 which is defined by the top side, provided with the opening 56, of the rotary element 24 and by a lip 70 extending around the inside of the hollow cylindrical rotary element 24 (FIG. 5). The rotary element 24 is then brought into a rotational position relative to the clamping element 22 which is such that the front side of the rotary element 24 which faces the clamping element 22 lies with its entire surface on the front side of the clamping element 22 which faces the rotary element 24. This is possible according to the embodiment under consideration as the inclination (or slope) of the oblique surface 52 of the rotary element 24 corresponds to the inclination (or slope) of the oblique surface 60 of the clamping element 22.

In order to prevent the clamping element 22 from unintentionally sliding in the direction of the diametrical widening 34 of the base body 20 (and therefore closing the openings 30, 32), the clamping element 22 is connected to the base body 20 by means of a gentle press fit. In other words, a certain force must firstly be exerted (by means of the rotary element 24) in the axial direction on the clamping element 22 in order for this to move (while overcoming the press fit) in the direction of the diametrical widening 34 of the base body 20 for fixing the traction element.

Figure 10:
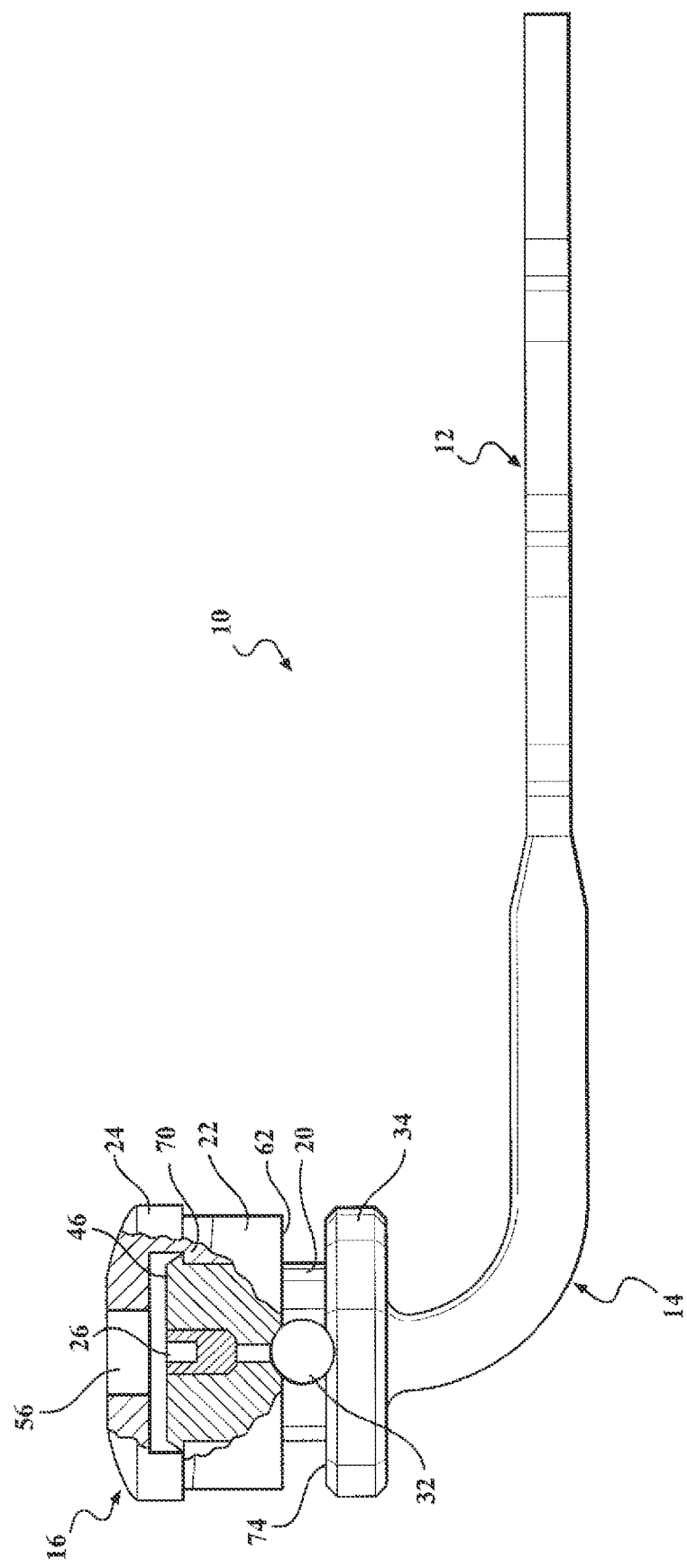
FIG. 10 is a side view of the finally assembled anchor device according to the first embodiment in a part-sectional view.

In order to permanently couple the rotary element 24 and therefore also the clamping element 22 to the base body 20, the locking bolt 26 is introduced through the opening 56 at the top side of the rotary element 24 into the axial opening 54 of the base body 20 in a final step. The two halves 40, 42 of the base body 20 and the respective part of the circumferential lip 46 which is formed thereon are moved away from one another as a result of the introduction of the locking bolt 26. On account of this radially outward movement of the circumferential lip 46, the lip 46 at the base body 20 engages behind the circumferential lip 70 inside the rotary element 24, whereby the base body 20 and the rotary element 24 are permanently connected together. These circumstances can be seen in FIG. 10 in a part-sectional representation. FIG. 10 shows the anchor implant 10 in the delivery state as assembled in the factory.

The anchor implant 10 according to the first embodiment operates as follows. In a first step the anchor implant 10 is fixed to a bone in the mouth region. For this purpose the anchor implant 10 is appropriately positioned and then fastened to the bone by means of preferably two or three bone screws. A traction element such as, for example, a wire is then passed through one of the two openings 30, 32 of the base body 20.

The rotary element 24 is rotated clockwise in the embodiment by means of a suitable tool in order to fix the traction element which is passed through one of the openings 30, 32. A rotation of the rotary element 24 clockwise causes the oblique surface 52 of the rotary element 24 to run onto the opposite oblique surface 60 of the clamping element. As the clamping element 22 is supported in a non-rotatable manner, it cannot rotate with the rotary element 24, but is instead moved in the axial direction towards the diametrical widening 34 on account of the co-operation of the two oblique surfaces 52 and 60. The clamping element 22 is therefore advanced up to the traction element disposed in one of the openings 30, 32. This advance movement causes the clamping element 22 (or the milled-out parts 64 thereof) to finally come into contact with the traction element which is to be fixed. Further rotation of the rotary element 24 after contact is established between the clamping element 22 and the traction element causes the traction element to be clamped so as to fix it relative to the anchor device 10.

The traction element may then be connected, e.g. to a tooth or to a retaining element which is fastened to a tooth. Depending on the orthodontic procedure which is used, it would also be possible to couple the traction element indirectly or directly to the tooth which is to be treated in a first step and only to fasten it to the anchor device 10 in a second step.

According to an alternative mode of use, a fastening element which is bent in the shape of a loop or is in the shape of a band can be suspended in the groove 74 represented in FIG. 10 between the diametrical widening 34 of the base body 20 and the planar front side 62 of the clamping element 22. The rotary element 24 may then optionally be actuated as explained above in a next step in order to clamp the traction element between the diametrical widening 34 and the planar surface 62. A loop- or band-shaped traction element may also be suspended in the circumferential groove 74 of the head 16 for orthodontic purposes without the rotary element 24 having to be actuated, i.e. without the traction element being clamping between the clamping element 22 and the diametrical widening 34.

It is obvious to the person skilled in the art that the anchor device 10 which is illustrated with reference to FIGS. 1 to 10 would also function with only slight alterations if just one oblique face were present. Thus, according to a first variant, the clamping device 22 could be completely omitted and the hollow cylindrical portion 50 of the rotary element 24 prolonged in the direction of the diametrical widening 34 of the base body 20. The rotary element 24 (or to be more precise the oblique surface 52 thereof) would then co-operate directly with a portion of the traction element which is to be clamped upon rotating the rotary element 24.

According to a second variant, the clamping element 22 could be retained, yet the hollow cylindrical structure 50 of the rotary element 24 replaced by just one tooth or a plurality of teeth running onto the oblique surface 60 of the clamping element 22 upon actuating the rotary element 24. Should a plurality of such teeth be provided, these could be of a height which varies in the circumferential direction of the rotary element 24 (in which case a bevelled structure comparable with the hollow cylindrical structure 50 could in turn be produced as the "envelope" of the teeth).

Figure 11:
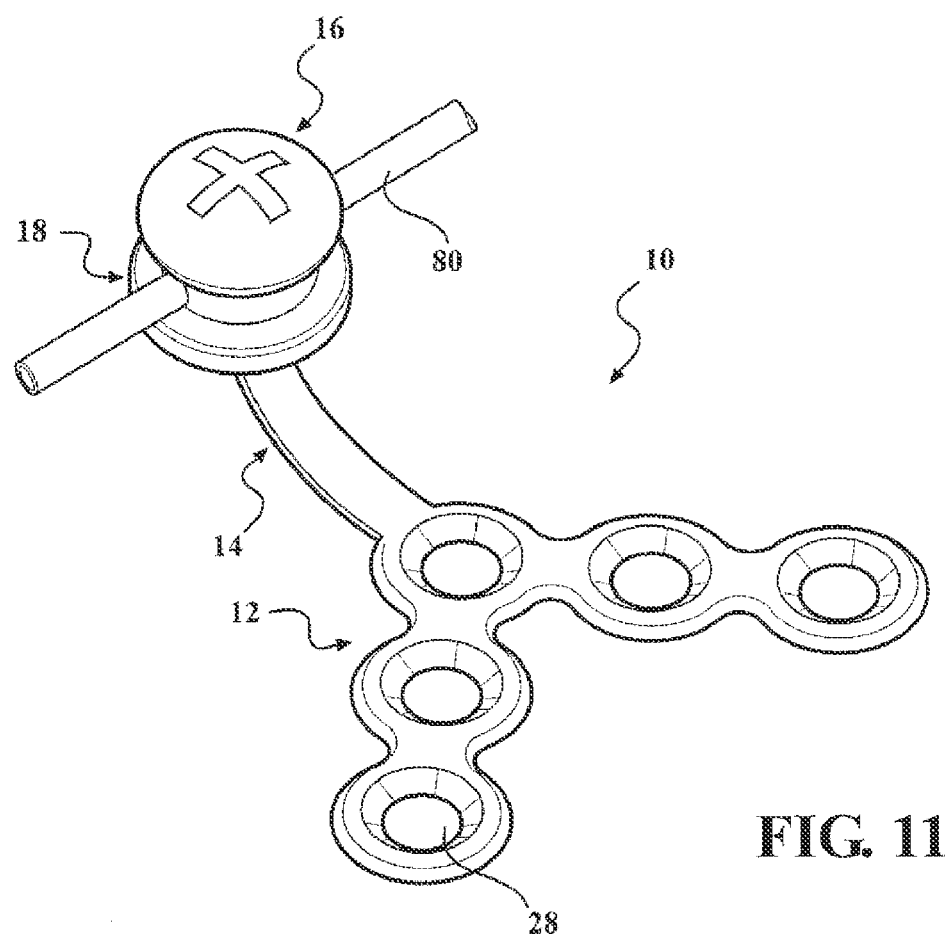
FIG. 11 is a perspective view of an anchor device according to a second embodiment of the invention with located traction element.
Figure 15:
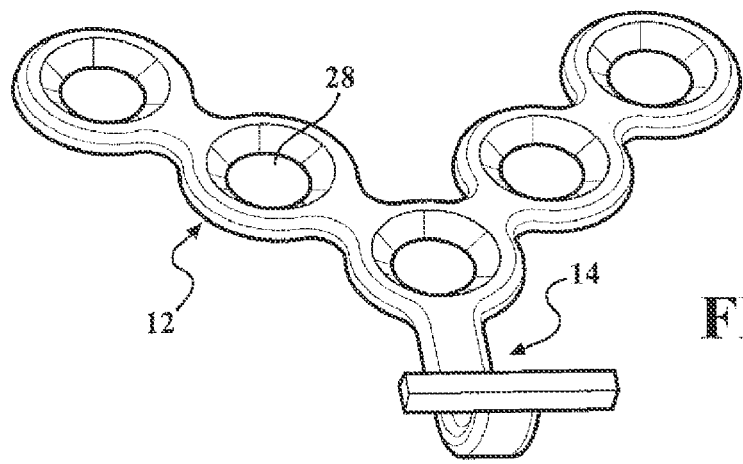
FIG. 15 is a perspective view of the fixing device, formed as a bone plate, of the anchor device according to FIG. 11.

A second embodiment of an anchor device 10 according to the invention is represented in FIGS. 11 to 15. The anchor device 10 according to the second embodiment has many features in common with the anchor device according to the first embodiment. For example, the fixing device is again a bone plate 12, although this has a V-shaped form. In other words, the total of five through-openings 28 of the bone plate 12 are disposed in the shape of a V. These circumstances are represented in FIGS. 11 and 15.

The bone plate 12 is connected by means of a stem-shaped intermediate piece 14 to a head 16, at which a clamping device 18 is in turn formed. The clamping device 18 serves to fasten a wire-shaped traction element 80 to the head 16 of the anchor device 10.

The clamping device 18 comprises openings 30, 32 formed in a base body 20 of the head 16 for locating the traction element 80 as well as an oblique surface 52, which is formed in the region of a rotary element 24. The rotary element 24 is provided with a cross recess structure 82 at its top side. A torque can be introduced into the rotary element 24 by means of the cross recess structure 82 for clamping the traction element 80. Whereas the base body 20 coupled to the intermediate piece 14 bent in the shape of an L has substantially the same structure and the same mode of operation as the base body of the anchor device according to the first embodiment, the rotary element 24 differs both structurally and functionally from the rotary element of the first embodiment.

Figure 13:
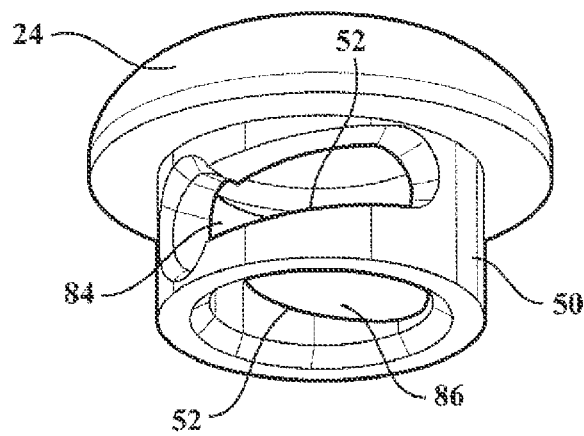
FIG. 13 is a perspective view of a rotary element of the anchor device according to FIG. 11.
Figure 14:
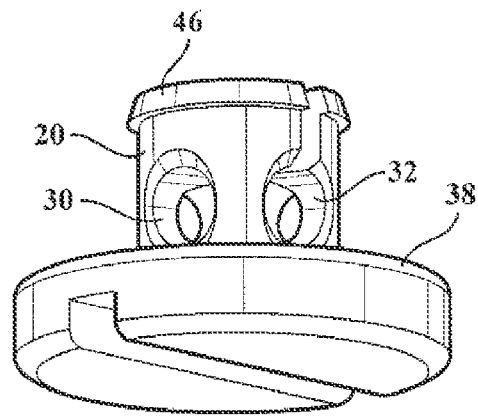
FIG. 14 is a perspective view of a head base body of the anchor device according to FIG. 11.

As can be seen from FIG. 13, the rotary element 24 has a hollow cylindrical structure 50, in the shell or mantle of which a respective opening 84, 86 is formed on two opposite sides. Each of the two openings 84, 86 is in the form of a slot or elongate hole extending obliquely (like a helix or helix portion). Obliquely extending surfaces 52 are formed by the inner lower front faces of these openings 84, 86, which surfaces allow the traction element 80 which is introduced into one of the openings 30, 32 to be fixed in a clamping manner.

In order to assemble the anchor device 10 according to the second embodiment, the base body 20 is welded in a first step to the intermediate piece 14 (which is integral with the bone plate 12) bent in the shape of an L. The rotary element 24 is then mounted on the base body 20. As it is mounted a lip 46, extending in the circumferential direction, of the base body 20 engages behind lips (not represented) which are disposed inside the rotary element 24 in a manner similar to that described for the first embodiment. A detent connection is thus formed.

Figure 12:
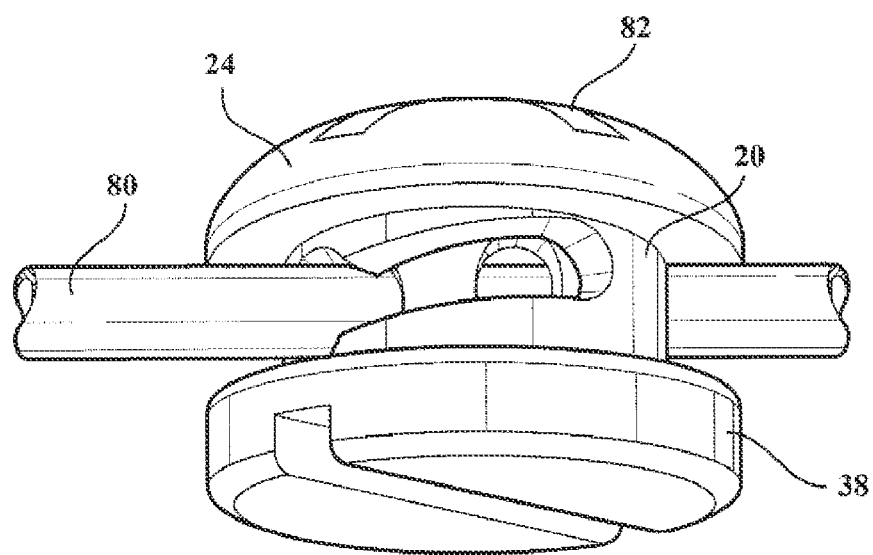
FIG. 12 is a side view of a head of the anchor device according to FIG. 11.

In order to fasten the traction element 80 to the anchor device 10 according to the second embodiment, the rotary element 24 is oriented relative to the openings 30, 32 in the base body 20 in a first step such that the traction element 80 can be passed unimpeded through one of the openings 30, 32. These circumstances are represented in FIG. 12. A torque is then introduced clockwise into the rotary element 24 by means of a Phillips-type screwdriver. This torque cause the oblique surfaces 52 to move in each case like a wedge on opposite sides of the corresponding opening 30, 32 between the traction element 80 fixed inside the opening 30, 32 on one side and a diametrical widening 38 of the base body 20 on the other. The traction element 80 is as a result fixed in a clamping manner between a (top in FIG. 12) boundary of the respective opening 30, 32 on one side and the oblique surface 52 of the rotary element 24 on the other.

The anchor devices according to the invention which have been described with reference to the preceding embodiments allow traction elements to be reliably fixed to the anchor device. The provision of at least one oblique surface, combined with a rotary mechanism, allows the traction element to be fixed in a simple and yet reliable manner. When compared with conventional techniques, such as the use of a clamping screw, the approach according to the invention has the advantage that only a slight rotational movement of often less than 90° is required to activate the clamping connection. This shortens the duration of the oral surgical operation.

Although the invention has been illustrated in the light of various embodiments, innumerable modifications or alterations and additions are conceivable. The invention is therefore solely limited by the scope of the claims that follow.

The invention claimed is:

1. A device for anchoring a first surgical traction element in the mouth region, comprising:
   a fixing device, which can be fixed in or to a bone; and
   a clamping device, coupled to the fixing device, with at least one locating region for the first surgical traction element and with an oblique first surface which is rotatable relative to the locating region or configured to co-operate with a rotary element for producing a clamping force which fixes the first surgical traction element upon a relative rotation of less than 90° taking place between the oblique first surface and one of the locating region and the rotary element, wherein the oblique first surface is formed in a region of a front face of a structure defined about an axis and which is one of substantially annular, cylindrical and hollow cylindrical, and wherein the oblique first surface extends in a circumferential direction of the structure about the axis over at most approximately 360° and comprises a slope that extends in the circumferential direction.

2. The device according to claim 1, wherein the clamping device has a second surface which extends obliquely to the first surface and co-operates with the first surface, wherein the first and the second surfaces are rotatable relative to one another to produce an advance movement giving rise to the clamping force.

3. The device according to claim 2, wherein the second surface is supported so as to be non-rotatable relative to the locating region.

4. The device according to claim 2, wherein the clamping device comprises a clamping element at which the second surface is formed.

5. The device according to claim 4, wherein the clamping element is disposed between the first surface and the locating region.

6. The device according to claim 4, wherein the clamping element has a form which is one of substantially annular, cylindrical and hollow cylindrical.

7. The device according to claim 1, further comprising a head which is retained by the fixing device and at which the clamping device is formed.

8. The device according to claim 7, wherein the head has a diametrical widening adapted to extend substantially parallel to the bone.

9. The device according to claim 4, wherein the head has at least one groove adapted to extend substantially parallel to the bone.

10. The device according to claim 9, wherein the groove extends in the circumferential direction of the head for suspending the first surgical traction element.

11. The device according to claim 9, wherein the locating region comprises the at least one groove.

12. The device according to claim 7, wherein the locating region comprises at least one opening passing through the head for at least one of introducing and passing through the first surgical traction element.

13. The device according to claim 1, wherein the fixing device comprises a bone plate with at least one through-opening for a fastening element.

14. The device according to claim 13, wherein the head extends substantially perpendicularly to the bone plate.

15. The device according to claim 13, wherein the bone plate has one of a T-, Y- and I-shaped form.

16. The device according to claim 1, wherein the fixing device comprises a bone screw thread.

17. The device according to claim 16, wherein the bone screw thread extends co-linearly with an axis of rotation of the relative rotation between the locating region, and the oblique first surface.

18. A bone anchoring system comprising:
    a first surgical traction element; and
    an anchoring device for anchoring the first surgical traction element in the mouth region, the anchoring device comprising a fixing component, which can be fixed in or to a bone and a clamping component, coupled to the fixing component, with at least one locating region for the first surgical traction element and with an oblique first surface which is rotatable relative to the locating region or configured to co-operate with a rotary element for producing a clamping force which fixes the first surgical traction element upon a relative rotation of less than 90° taking place between the oblique first surface and one of the locating region and the rotary element, wherein the oblique first surface is formed in a region of a front face of a structure defined about an axis and which is one of substantially annular, cylindrical and hollow cylindrical, and wherein the oblique first surface extends in a circumferential direction of the structure about the axis over at most approximately 360° and comprises a slope that extends in the circumferential direction.

19. The system according to claim 18, wherein the first surgical traction element is a wire.

20. The system according to claim 18, further comprising a second surgical traction element in the form of an elastic band or an elastic ring.

21. A device for anchoring a surgical traction element in the mouth region, comprising:
    a fixing device for securing to bone;
    a head disposed on the fixing device; and
    a clamping device coupled to the head and including:
       at least one locating region adapted to receive the surgical traction element;
       a rotary element disposed about a rotational axis and rotatable relative to the locating region; and
       an oblique surface, the rotary element having the oblique surface or co-operating with the oblique surface to produce a clamping force to secure the first surgical traction element upon relative rotation of less than 90° between the rotary element and the locating region,
       the rotary element being axially locked to the head such that the rotary element is axially restrained from movement in a direction away from the locating region while the rotary element is rotated relative to the locating region to produce the clamping force.

22. The device according to claim 21, wherein the oblique surface extends in a circumferential direction about the head over at most approximately 360° and the oblique surface comprises a slope that extends in the circumferential direction such that the oblique surface slopes toward and away from the locating region in the circumferential direction.

23. The device according to claim 21, wherein the clamping device further comprises a clamping element having an oblique second surface fixed from rotation relative to the locating region and which extends obliquely to the oblique first surface and co-operates with the oblique first surface, wherein the oblique first and the second surfaces are rotatable relative to one another to produce an advance movement giving rise to the clamping force.

24. The device according to claim 21, wherein the head has at least one groove adapted to extend substantially parallel to the bone and support the surgical traction element.

25. The device according to claim 21, wherein the locating region comprises at least one opening passing through the head for at least one of introducing and passing through the surgical traction element.

26. The device according to claim 21, wherein the fixing device comprises a bone plate with at least one through-opening for a fastening element.

* * * * *